US008021695B2

(12) United States Patent
Gruber

(10) Patent No.: US 8,021,695 B2
(45) Date of Patent: Sep. 20, 2011

(54) PERSONAL CARE COMPOSITION CONTAINING LEGHEMOGLOBIN

(75) Inventor: James V. Gruber, Somerville, NJ (US)

(73) Assignee: Arch Personal Care Products, L.P., South Plainfield, NJ (US)

( * ) Notice: Subject to any disclaimer, the term of this patent is extended or adjusted under 35 U.S.C. 154(b) by 936 days.

(21) Appl. No.: 10/366,231

(22) Filed: Feb. 13, 2003

(65) Prior Publication Data
US 2003/0198700 A1    Oct. 23, 2003

(51) Int. Cl.
*A01N 65/00*    (2009.01)
(52) U.S. Cl. ........................................................ 424/725
(58) Field of Classification Search .................. None
See application file for complete search history.

(56) References Cited

U.S. PATENT DOCUMENTS

| | | | | |
|---|---|---|---|---|
| 2,239,345 | A | 4/1941 | Sperti | 167/74 |
| 5,126,263 | A | 6/1992 | Cocking | 435/240.47 |
| 5,229,291 | A * | 7/1993 | Nielsen et al. | 435/252.2 |
| 5,371,089 | A | 12/1994 | Rattan | 514/261 |
| 5,602,139 | A | 2/1997 | Rattan | 514/261 |
| 6,160,021 | A | 12/2000 | Lerner et al. | 514/645 |
| 6,303,106 | B1 * | 10/2001 | Banister et al. | 424/62 |
| 7,141,083 | B2 * | 11/2006 | Jordan | 44/307 |
| 2003/0044783 | A1 * | 3/2003 | Williams et al. | 435/6 |

FOREIGN PATENT DOCUMENTS

| | | |
|---|---|---|
| EP | 0 673 643 | 9/1995 |
| FR | 2 616 659 | 12/1988 |
| FR | 2 641 463 | 7/1990 |
| JP | 7330579 | 12/1995 |
| JP | 10099044 | 4/1998 |
| JP | 2001511151 | 8/1998 |
| JP | 2000051322 | 2/2000 |
| SU | 411 867 | 1/1974 |
| WO | 99/11143 | 3/1999 |
| WO | WO 9913855 | 3/1999 |

OTHER PUBLICATIONS

Symbiotic Nitrogen Fixation, 2007, pp. 1-3, http://users.rcn.com/jkimball.ma.ultranet/BiologyPages/N/NitrogenFixation.html.*
Isolation and Identification of Endogenous Cytokinins from Alfalfa by Takeshi Hashizume et al., Agric. Biol. Chem. 1985: 49, pp. 3481-3484.
"Determination of the chemical structure of the capsular polysaccharide of strain B33, a fast-growing soya bean-nodulating bacterium isolated from an arid region of China" by Miguel A. Rodriguez-Carvajal et al., Biochem J., 2001, 357, pp. 505-511.
"The Antioxidants of Legume Nodule Mitochondria" by Inaki Iturbe-Ormaetxe et al., Mol. Plant Microbe Interact vol. 14 No. 10, 2001, pp. 1189-1196.
"Nitric Oxide in Human Skin: Current Status and Future Prospects" by Daniela Bruch-Gerharz et al., Journal of Investigative Dermatology, 1998, pp. 1-7.
"Purification of leghemoglobin from nodules of *Crotalaria* infected with *Rhizobium*" by Elenira H.M. Mendonca et al., Phytochemistry, 1999, vol. 50, pp. 313-316.
"Specific flavonoids induced nod gene expression and pre-activated nod genes of *Rhizobium leguminosarum* increased pea (*Pisum sativum* L.) and lentil (*Lens culinaris* L.) nodulation in controlled growth chamber environments" by Anjuman Ara Begum et al., Journal of Experimental Botany, Jul. 2001, vol. 52, No. 360, pp. 1537-1543.
"Nitric Oxide Produced by Ultraviolet-irradiated Keratinocytes Stimulates Melanogenesis" by Christine Romero-Graillet et al., Journal of Clinical Investigation, Feb. 1997, vol. 99, No. 4, pp. 635-642.
"Characterization of Recombinant Soybean Leghemoglobin *a* and Apolar Distal Histidine Mutants" by Mark S. Hargrove et al., Journal of Mol. Biol., 1997, vol. 266, pp. 1032-1042.

* cited by examiner

*Primary Examiner* — Michael Meller
(74) *Attorney, Agent, or Firm* — Wiggin and Dana LLP; Dale L. Carlson; Wanli Wu

(57) ABSTRACT

A personal care composition comprising leghemoglobin and at least one preservative selected from the group consisting of alcohols, glycols, parabens, hydantoins, quaternary nitrogen-containing compounds, isothiazolinones, aldehyde-releasing agents, and halogenated compounds. Preferably, the leghemoglobin is a nitrogen fixation root nodule extract providing a leghemoglobin concentration in the composition of between 0.0001% and about 10% based upon the total weight of the composition. Also disclosed is a method for preparing the personal care composition.

4 Claims, No Drawings

PERSONAL CARE COMPOSITION CONTAINING LEGHEMOGLOBIN

FIELD OF THE INVENTION

This invention relates generally to personal care compositions, and more specifically to such compositions containing leghemoglobin. The leghemoglobin is suitably extracted from nitrogen fixation root nodules. The leghemoglobin provides advantageous properties to the personal care composition during use by facilitating the control of reactive oxygen and nitric oxide free radicals on the skin.

BACKGROUND OF THE INVENTION

Personal care compositions encompass a wide variety of applications, including soaps, shampoos, skin care medicaments, cosmetics, as well as therapeutic and homeopathic skin care formulations. The use of plant-derived raw materials in personal care compositions is well established. By way of illustration, PCT patent publication WO 9913855 discloses the use of a combination of algae extract and exopolysaccharides for cosmetic and dermapharmaceutical applications.

Consideration of the use of plant-derived materials in personal care has become especially important in view of the recent discovery that certain animal-borne diseases, such as Bovine Spongiform Encephalopathy (BSE), are spread to humans through contact with infected meat and meat by-products. The sensitivity of the personal care industry to these issues is so great that even the sale of lanolin, a by-product derived from the shearing of sheep wool, has suffered because it is considered to be an animal-derived product.

The use of human-derived ingredients in personal care compositions is also frowned upon for the same reasons as suggested above for animal-derived products. Human-derived products can have even greater concerns than animal-derived constituents because pathogens borne in the human-derived cosmetic ingredients are even more likely to have a detrimental effect on human health. It has been suggested, for example, in U.S. Pat. No. 6,160,021 that human derived blood constituents, such as hemoglobin, when administered topically can influence the production of melanin in the skin providing a method of skin lightening.

As a consequence of these market pressures, personal care composition manufacturers are relying more heavily on plant-derived raw materials, such as plant proteins obtained from corn, soy and wheat replacing animal proteins. In addition, the cosmetic and personal care industries look closely to the health food and herbal supplement industries for trends in product development. Such trends are summarized, for example, in a recent article in *HAPPI* 38 (2001) 81. This article summarizes many of the pressures that face global cosmetic raw material manufactures and the recent trends towards 'natural' based products. Good examples of this are the recent trends of aromatherapy and natural extracts, particularly plant extracts, as useful ingredients for providing functionality and support the labeling claims as to such 'natural' based personal care products.

Several plants have enjoyed a healthy growth in personal care compositions because of their purported benefits to humans. For example, Aloe Vera is a well-known plant that provides an extract that is known to help aid wound healing. Gingo biloba and grapes are known to contain polyphenols that are purported to provide anti-oxidative effects to human skin, ameliorating the harmful effects of UV damage on the skin. Soybean extracts are extremely popular due to the presence of soy isoflavones that are suggested to contain plant phytoestrogens, compounds that mimic human estrogen and help ameliorate the effects of aging, particularly in post-menopausal women. Products such as extracts from *Asafaetida* and Yellow dock are suggested, for example, to minimize excess melanin formation that is responsible for the appearance of age spots on the skin. Recently, U.S. Pat. Nos. 5,371,089 and 5,602,139 disclose that plant growth regulators known as cytokinins appear to extend the longevity of human fibroblasts, the cells from which human keratinocytes arise. Keratinocytes become the protective cells that comprise the stratum corneum and make human life possible on this planet. Certain bacterial and yeast extracts are known to provide useful cosmetic, therapeutic or homeopathic effects, in particular, yeast such as *Saccharomyces cerevisiae*. In addition, some root extracts, for example, ginseng, have carried a historical trend for health and energy and are seen to appear in personal care products purporting such claims.

A major component of the atmosphere surrounding the earth is nitrogen gas, $N_2$. Both plants and animals are bathed in nitrogen gas from the air and yet, because of the extraordinary chemical stability of this molecule, nitrogen gas is essentially chemically inert to both plants and animals. However, molecular nitrogen is a key component of all of the amino acids, vitamins, proteins, enzymes, and cells of both Kingdoms. Without a means for converting nitrogen gas into useful nitrogen components such as ammonia, life as we know it on this planet would not exist. The conversion of nitrogen gas into useful nitrogen substrates occurs through natural and industrial means and comprises what is known as the nitrogen cycle.

Fortunately, while plants and animals are incapable of chemically converting nitrogen into useful nitrogen-containing components, certain bacteria, especially those of the blue-green Cyanobacteria Kingdom, such as, for example, *Rhizobium*, have evolved a mechanism to convert nitrogen into more useful ammonia. The process of conversion is known as 'Nitrogen Fixation' and relies on the presence in these organisms of a key enzyme known as nitrogenase.

Nitrogen fixation is a complex enzymatic process. The general enzymatic reaction to convert nitrogen into ammonia can be summarized as:

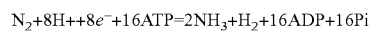

$$N_2 + 8H + + 8e^- + 16ATP = 2NH_3 + H_2 + 16ADP + 16Pi$$

The process is intimately driven by conversion of adenosine triphosphate, ATP, into adenosine diphosphate through reduction of nitrogen to ammonia by nitrogenase enzyme. Because the reaction is a reduction reaction, it is very sensitive to the presence of oxygen.

Some free-living organisms, such as lichen, are capable of fixing nitrogen but typically on a very small scale. Interestingly, *Rhizobium* bacteria, however, will not convert nitrogen into ammonia when they exist alone. The bacteria are generally unable to keep the oxygen away that is detrimental to the overall nitrogen fixation reaction. In order to overcome this problem, the bacteria have evolved an unusual associative relationship with many green plants. The bacteria, which can be found readily in the soil, will infect the roots of various plants, in particular, the roots of legumes, for example. The bacteria are attracted to the roots by the excretion of various flavonoids such as luteolin and hesperetin, such flavonoids being referenced, for example, in Begum, A. A. et. al., *J. Exper. Bot.* 2001; 52, 1537-1543 the contents of which is incorporated in its entirety into the body of this invention.

Once within the roots of the plants, the bacteria force plants to build small, oxygen deficient homes known scientifically as symbiosomes and more commonly as 'root nodules' in which the bacteria can live and carry out the nitrogen fixation reaction. The plant, however, does not suffer from the infection, but instead benefits from the bacterial conversion of nitrogen into ammonia by using the ammonia for its own life processes. This relationship between the blue-green bacteria and the green plant is symbiotic. That is, both organisms benefit from the relationship. The seeds of many commercial crops that provide safe havens for nitrogen fixing bacteria are actually sold commercially with the fixing bacteria mixed with the seeds prior to planting. Such combinations can be found, for example, at commercial websites such as that provided for Agrobiologicals at http://www.agrobiologicals.com/glossary/Cont6.htm.

The bacteria build the root nodule by infecting the root hairs of the green plant and switching on the plant growth regulators that cause a rapid growth of plant cells around the infected site. The bacteria control the growth of the nodule by taking over the localized growth mechanisms of the root by using various plant growth regulators such as, for example, cytokinins as well as important complimentary plant growth regulators such as auxins, such plant growth regulators being referenced, for example in Schultze, M. et. al., *Anna. Rev. Genet.* 1998; 32, 33-57 incorporated in its entirety into the body of this invention. In addition, the bacteria begin expanding in size and shedding their cells walls, becoming bacteroids that begin forming a biofilm-like lining around themselves made from excreted lipopolysaccharides, exopolysaccharides and capsular polysaccharides that further prevents the infiltration of oxygen into the nodule. Such polysaccharides are referenced, for example in Rodriquez-Carvajal, M. A. et. al., *Biochem. J.* 2001; 357, 505-511 incorporated in is entirety into the body of this invention. Because the process of nitrogen fixation is so sensitive to the presence of oxygen and reactive oxygen radicals, the root nodule bacteria also accumulate and produce a variety of anti-oxidants including but not limited to, for example, peroxidases, superoxide dismutases, glutathiones, catalases, oxidases and other protective enzymes and molecules as might be found described in, for example, Iturbe-Ormaetxe, I. et. al., *Mol. Plant. Microbe Interact.* 2001; 14, 1189-1196 incorporated in its entirety into the body of this invention.

As a further defense mechanism, the bacteria begin to produce a protein known as 'leghemoglobin' that behaves much like human hemoglobin. The human body has four important globin molecules (distinguished by the presence of a heme-based porphyrin ring at the active site of the protein). These include myoglobin, neuroglobin, hemoglobin and a recently discovered fourth globin called histoglobin. Globin proteins are distributed throughout the human body where they capture and control oxygen reactive molecules such as $O_2$, $CO_2$, and NO (nitric oxide). In the symbiosomes, oxygen will bind to the leghemoglobin and is removed, through an oxygen transport mechanism, thus further improving the anaerobic conditions the bacteria require for the nitrogen fixation reaction to occur.

The interior of the nitrogen fixation nodule, therefore, is a complex mixture of plant growth regulators, amino acids, vitamins, proteins, polysaccharides, minerals and enzymes all which are either helping the plant grow, protecting or nourishing the bacteria. The composition of most of these root nodule extracts is also regionally controlled due to the soil and climates in which the individual plants are grown. However, regardless of the source of the plant, the climate or other factors, active root nodules will always contain leghemoglobin and nitrogeneased.

In addition to binding oxygen, it has recently been established that globin-type proteins, such as hemoglobin, myoglobin and leghemoglobin, will bind nitric oxide (see for example, Hargrove, M et al., *J. Mol. Biol.* 1997; 266: 1032-1042). Nitric oxide has been found to be a potent controller of human blood flow (see, for example, Stix, G. *Scientific American* 2001, November). It has also become well established that an enzyme called nitric oxide synthase controls the presence of nitric oxide in the skin. Nitric oxide has been found to be part of the biochemical cascade that occurs in skin when the skin becomes irritated (see, for example, Bruch-Gerharz, D., et. al., *J. Invest. Dermatol.* 1998; 110:1-7). In particular, the presence of nitric oxide free radicals in the skin has been demonstrated, along with the free radicals derived from oxygen such as, for example, hydrogen peroxide, to have detrimental effects on the health of the skin (see, for example, Hurling, T. et. al., *SOFW J.* 2000; 126: 20-26). Accordingly, treatments to reduce nitric oxide levels on the skin have been disclosed in the literature. Illustratively, U.S. Pat. No. 6,160,021 discloses, at column 3, lines 28-45 thereof, a skin-treatment method for decreasing the level of nitric oxide by administering to the skin, either topically or subcutaneously, an inhibitor of NO synthase or an NO scavenger, such as a heme compound, such as hemoglobin.

In addition, it has recently been recognized that nitric oxide radicals appear to also be responsible for the initiation of the cascade that causes melanogenesis in human melanocytes. It has been suggested, for example, that human-derived hemoglobin can control the production of tyrosinase in fibroblasts as suggest in, for example, Romero-Graillet, C. et al., *J Clin Invest.*, 1997; 99: 635-642, incorporated in its entirety in the body of this invention. Therefore, the control and modulation of oxygen and nitric oxide free radicals in the skin remains an area of considerable commercial and academic interest and research.

Plants can be grown and removed from the soil to expose the root nodules. Interestingly, the contents of the nitrogen fixation nodules can be extracted using various methods of extraction well known to those skilled in the art. Such examples may comprise simple aqueous extractions as, for example, discussed on the Reed College website under "Nitrogen Fixation. Part II. Physiology and Anatomy of Nitrogen Fixation" found at http://web.reed.edu/academic/department/biology/nitrogen/Nfix2.html, or they may be more complex extractions as described, for example, in Mendonca, E H M. et. al., *Phytochemistry* 1999; 50: 313-316. In addition, the extractions may involve the use of super critical carbon dioxide extraction, methods of which are known to those skilled in the art. These extractions will comprise a mixture of the plant growth regulators, amino acids, vitamins, proteins, polysaccharides, minerals and enzymes that comprise the root nodules.

BRIEF SUMMARY OF THE INVENTION

In one aspect, the present invention relates to a personal care composition comprising leghemoglobin and at least one preservative selected from the group consisting of alcohols, glycols, parabens, quaternary nitrogen-containing compounds, isothiazolinones, aldehyde-releasing agents, antioxidants and halogenated compounds, such preservatives being found listed, for example, in Steinberg, D. C. *Cosmet. Toilet.* 1997; 112, 57-65, the contents of which is incorporated in it entirety into the body of this invention. Preferably, the leghemoglobin is a nitrogen fixation root nodule extract providing a leghemoglobin concentration in the composition of between 0.0001% and about 10% based upon the total weight of the composition.

In another aspect, the present invention relates to a method for preparing a personal care composition comprising the steps of:

(a) extracting the leghemoglobin from root nodules infected with bacteria selected from the group consisting of Cyanobacteria, Anaerobic bacteria, Purple sulfur bacteria, Purple non-sulfur bacteria, Green sulfur bacteria, legumes bacteria, and combinations thereof, in order to provide a leghemoglobin extract, and (b) combining the leghemoglobin extract with a preservative to provide the personal care composition.

In yet another aspect, the present invention relates to a method for binding free radicals on the skin that comprises contacting the skin with leghemoglobin, thereby causing said leghemoglobin to act as a scavenger for the free radicals.

These and other aspects will become apparent upon reading the following detailed description of the invention.

DETAILED DESCRIPTION OF THE INVENTION

It has now been now surprisingly found that the extracts of roots nodules from various plants, for example, perennial legumes such as peas, beans, and soybeans, annual legumes such as clover and alfalfa, and woody legumeous plants such as Australian Pine, contain leghemoglobin, as well as many other useful components, that provide advantages when incorporated into personal care compositions. The other useful components of the extracts comprise, for example, plant growth regulators, amino acids, vitamins, proteins, polysaccharides, minerals and enzymes. Additionally, these extracts can function as part of a growth media for other organisms such as, for example, yeast such as *Saccharomyces cerevisiae*, providing key growth factors to these organisms that can then be further extracted for use in personal care compositions. Moreover, one or more components of these extracts is suitably encapsulated within, for example, liposomes, niaosomes, sub-micron emulsions, polymeric encapsulants, gels, creams or lotions, to provide a time-release property to the extract components. Moreover, some of the extract components, notably leghemoglobin, bind to oxygen and nitric oxide in the skin, effectively controlling the presence of these molecules, and minimizing the formation of free radicals.

Without wishing to be bound by any particular theory, the present inventor postulates that the presence of leghemoglobin, topically applied to the skin, will bind to oxygen and nitric oxide present in the skin, effectively removing these molecules from their normal radical breakdown cycles and thus, effectively eliminating the detrimental effects of their free radicals on the skin. Without being further bound by theory, the inventor suggests that leghemoglobin can remove nitric oxide from binding with other critical heme-based enzymes such as, for example, guanylyl cyclase, the enzyme responsible for upregulating the production of cyclic-GMP, in a competitive fashion effectively slowing significant biochemical pathways in human cells dependent on the upregulation of c-GMP.

The nitrogen fixation root nodule extracts of the present invention can be obtained from any number of microorganisms as summarized, for example, in a table provided on The University of Edinburgh's website under the heading "The Microbial World. The Nitrogen Cycle and Nitrogen Fixation" found on their website located at http://helios.bto.ed.ac.uk/bto/microbes/nitrogen.htm, and incorporated herein by reference in its entirety. Illustrative origins include, for example, aerobic bacteria such as those from the Genus' *Azotobacter, Beijerinckia, Klebsiella* and other Cyanobacteria, anaerobic bacteria such as, for example, organisms from the Genus' *Clostridium, Desulfovibrio*, Purple sulfur bacteria, Purple non-sulfur bacteria and Green sulfur bacteria, bacteria that inhabit legumes such as, for example, bacteria from the Genus *Rhizobium* and *Brachyorhizobium* and bacteria that infect other types of plants such as, for example, bacteria from the Genus *Frankia* and *Azospirillum*. Especially preferred are the nitrogen fixation root nodule extracts from the *Rhizobium* and *Brachyorhizomium* bacteria that infect annual and perennial legumes, in particular soybean root nodule extracts.

Plants from which the root nodules might be taken can include a variety of species found around the planet. Such plant species can include, but are not limited to, those listed in the article by Lindermann, W. C. and Glover, C. R., entitled "Nitrogen Fixation by Legumes" found at http://iubio.bio.indiana.edu/R35541-209718-/news/bionet/biology/n2-fixation/9702.newsm and included in its entirety in the body of this invention. Such plants might include, for example, perennial legumes such as alfalfa, sweetclover, vetches and true clover or annual legumes such as, for example, beans, faba beans, peas, cowpeas, peanuts and soybeans. Certain legumeous woody plants are known to carry nitrogen fixation bacterial infections such as, but not limited to, Australian pine. Especially preferred are the root nodules found on soybeans.

The personal care composition of the present invention suitably contains leghemoglobin and at least one preservative selected from the group consisting of alcohols, glycols, parabens, quaternary nitrogen-containing compounds, isothiazolinones, aldehyde-releasing agents, antioxidants and halogenated compounds. Illustrative alcohols include phenoxyethanol, isopropyl alcohol, and benzyl alcohol; illustrative glycols include propylene, butylene, and pentylene glycol; illustrative parabens (also known as parahydroxybenzoic acids) include methyl, propyl and butyl-parabens; illustrative quaternary nitrogen-containing compounds include, benzalkonium chloride, and Quaternium 15; illustrative isothiazolinones include methylisothiazolinone and methylchloroisothiazolinone; illustrative aldehyde-releasing agents include DMDM hydantoin, imidazolidinyl urea and diazolidinyl urea; illustrative antioxidants include butylated hydroxytoluen and tocopherol, and illustrative halogenated compounds include triclosan, and chlorohexidine digluconate.

Additionally, the personal care composition can optionally contain other functional ingredients such as, for example, water, surfactants, emulsifiers, conditioners, emollients, waxes, oils, polymers, thickeners, fixatives, colorants, humectants, moisturizers, stabilizers, diluents, solvents, fragrances and the like, as well as active ingredients such as, for example, botanicals, neutraceuticals, cosmeceuticals, therapeutics, pharmaceutics, antifungals, antimicrobials, steroidal hormones, antidandruff agents, anti-acne components, sunscreens, preservatives and the like. The concentration of the root extract component or components in the cosmetic composition is suitably in the range of 0.0001% to 99% by weight, preferably between 0.1% and 10%, based upon the total weight of the cosmetic composition. The composition of the present invention can be used in various types of cosmetic formulations including, but not limited to, lotions, ointments, creams, sprays, spritzes, aqueous or aqueous alcoholic mixtures, gels, mousses, patches, pads, masks, moistened cloths and wipes, solid sticks, clear sticks, lipsticks, aerosol creams, anhydrous powders, talcs, tonics, oils, emulsions, and bath salts.

The root nodule extracts can be obtained from the roots by a variety of extraction methods known to those skilled in the art. Such extracts may involve the use of water, water miscible organic solvents such, for example, acetone, butylenes glcyol or ethanol, or organic solvents such as, but not limited to, hexane or methyl ethyl ketone. The extraction may also involve the use of supercritical fluid extraction, such as, but not limited to, super critical carbon dioxide extraction. The root nodules may be found to occur in a moistened state or a dried state, such conditions influencing the final composition of the extract, but not the method of extraction. The root nodule extraction may be done alone, or in the presence of other plant components such as leaves, stems, flowers, seeds and roots. The presence of these components can modify the resulting extraction composition. The extraction can be conducted at normal atmospheric pressure or under greater or lesser pressures depending on the method of extraction. The extraction can be conducted at temperatures between −30° C. and 200° C., more preferably between 5° C. and 100° C., most preferably between 25° C. and 45° C., such extraction solvents, pressures and temperatures being suitably selected so as to not denature the leghemoglobin proteins found in the root nodule extracts.

The extracts of the present invention may be further purified by any number of means known to those skilled in the art including, but not limited to, chromatography, steam distillation, solvent extraction, centrifugation, decantation, filtration, or carbon treatment. The extracts of the present invention may be further concentrated by any means known to those skilled in the art including, but not limited to, evaporation, spray-drying, lyophylization, steam distillation or belt or drum drying.

The following Examples are intended to illustrate the art of the present invention and are not intended to limit the scope of the claims below.

EXAMPLE 1

Two kilograms of freshly pulled soybean (*Glycine max*) plants including the roots were washed with a gentle stream of deionized water to remove residual soil. The nitrogen fixation nodules, which were readily apparent on well-infected roots, were easily removed by hand and were collected. To approximately 100 grams of isolated nodules was added 200 mls of deionized water and the entire mixture was macerated in a Waring blender at high shear. The resulting dark heterogeneous lysate was filtered through cheesecloth to remove large pieces of undissolved material. The resulting hazy, dark solution was further purified by filtration through fine filter paper and by carbon and sterile filtration that removed the organisms responsible for a strong earthy odor in the extract.

The level of leghemoglobin in this particular extract was found to be approximately 0.3 mg/ml as determined by the following analysis method. To a 10 ml sample of the extract was added 1 ml of 0.1M sodium dithionite in 0.1 M Potassium Phosphate Buffer Solution (PBS) at pH 7.0. This sample was treated with gaseous carbon monoxide (CO) by gently bubbling a stream of the gas into the sample for 20 minutes. This procedure permanently binds carbon monoxide to the heme iron of the leghemoglobin providing a leghemoglobin-CO complex (referred to as Lba-CO) that has an extinction coefficient of 200 mM$^{-1}$ cm$^{-1}$ at 416 nm wavelength in the ultraviolet spectrum. Using 0.4 ml of the Lba-CO complex solution in a 1-cm pathlength UV cuvette and comparing it an absorbance blank of PBS at pH 7.0 one determines the concentration of leghemoglobin using the resulting absorbance and the known extinction coefficient for the Lba-CO complex.

EXAMPLE 2

Two kilograms of roots containing active nitrogen fixation nodules were obtained from Lotus plant (*Lotus japonicus*) grown hydroponically in vermiculite inoculated with bacteria from the Genus *Brachyorhizobium*. Approximately 100 grams of the nitrogen fixation nodules were cleaned and removed and the resulting nodules were extracted by macerating the nodules in a Waring blender with 200 mls of 80% aqueous ethanol. The resulting heterogeneous mixture was filtered as described above. The ethanol was removed via low temperature vacuum evaporation and replaced with a comparable amount of deionized water providing a root nodule extract containing approximately 0.6 mg/ml of leghemoglobin as analyzed using the method described in Example 1.

EXAMPLE 3

Samples of root nodules obtained from Alfalfa (*Medicago sativa*) were treated in a similar fashion as described above in Example 1. HPLC analysis of these extracts for the presence of the cytokinins zeatin (a pure sample of zeatin was obtained from Serva (Islandia, N.Y.) provided concentrations comparable to those reported in the literature, in particular, Hashizume, T. et al., *Agric. Biol. Chem.* 1985; 49: 3481-3484. The extract was analyzed using the method described in Example 1 and was found to comprise approximately 0.5 mg/ml of leghemoglobin.

EXAMPLE 4

An aqueous extract was prepared from root nodules harvested from the plant Lupine (*Lupinus* ?) using the method described in Example 1. This extract was found to contain 0.4 mg/ml of leghemoglobin.

EXAMPLE 5

Samples of the various aqueous root nodule extracts were incorporated into a liposome comprising phospholipid and lecithin obtained from soybean beans. The extract was slurried together with the phospholipid and lecithin components and the mixture was homogenized using a high-pressure homogenizer obtained from Hydraulic Engineering Corporation (Brea, Calif.). The milky white mixture contained the nitrogen fixation root nodule extract encapsulated with the liposomal components.

EXAMPLE 6

A 1:1 mixture of the root nodule extract from Example 1 and a mixture of maltodextrin encapsulating oligosaccharides available as a 67% mixture of maltodextrin sugars and water from Roquette America (Keokuc, Iowa) was spray-dried using a commercial spray dryer. The resulting encapsulated powder contained approximately 0.15 mg/ml of leghemoglobin as determined by taking a sample and redissolving it in water and analyzing the mixture for leghemoglobin using the method described in Example 1.

EXAMPLE 7

A sample of the aqueous soybean root nodule extract from Example 1 was placed into an aqueous mixture of Baker's Yeast growth media obtained from Red Star Yeast (Milwaukee, Wis.). The media was inoculated with an active yeast culture also obtained from Red Star and the mixture was allowed to ferment under controlled aerobic conditions to provide a Live Yeast Cell Derivative (LYCD) obtained using stress conditions as described in U.S. Pat. No. 2,239,345. The resulting yeast lysate continued to test positive for the presence of leghemoglobin as demonstrated by using the method referenced in Example 1.

Examples 8-11 illustrate skin care compositions according to the present invention that can be prepared using various root nodule extracts as disclosed in examples 1-4.

EXAMPLE 8

This example illustrates a high internal phase water-in-oil emulsion incorporating the root nodule extract prepared as disclosed in Example 1.

| Ingredient | wt % |
| --- | --- |
| 1,3-dimethyl-2-imidazolidinone | 0.2 |
| Brij 92[1] | 5.0 |
| Bentone 38 | 0.5 |
| $MgSO_4 \cdot 7H_2O$ | 0.3 |
| DMDM Hydantoin | 0.01 |
| Root Nodule Extract | 10.0 |
| Water | to 100 |

[1]Brij 92 is polyoxyethylene (2) oleyl ether

EXAMPLE 9

This example illustrates an oil-in-water cream incorporating the root nodule extract prepared as disclosed in Example 4.

| Ingredient | wt % |
| --- | --- |
| Mineral Oil | 4 |
| 1,3-dimethyl-2-imidazolidinone | 1 |
| Brij 56[1] | 4 |
| Alfol 16RD[2] | 4 |
| Triethanolamine | 0.75 |
| Butane-1,3-diol | 3 |
| Xanthan gum | 0.3 |
| Methyl, Propyl and Butyl Paraben | 0.01 |
| Root Nodule Extract | 10.0 |
| Water | to 100 |

[1]Brij 56 is cetyl alcohol POE (10)
[2]Alfol 16RD is cetyl alcohol

EXAMPLE 10

This example illustrates an alcoholic lotion incorporating a root nodule extract prepared as disclosed in Example 2.

| Ingredient | wt % |
| --- | --- |
| 1,3-dimethyl-2-imidazolidinone | 0.3 |
| Ethanol | 40 |
| Root Nodule Extract | 10.0 |
| Water | to 100 |

EXAMPLE 11

This example illustrates a sub-micron emulsion concentrate that contains a root nodule extract prepared as described in Example 3.

| Ingredient | wt % |
| --- | --- |
| Trimethylolpropane Tricaprylate/Tricaprate | 18.0 |
| Glycerin | 8.0 |
| Cetearyl alcohol | 2.0 |
| Ceteareth 20 | 2.0 |
| Glyceryl stearate | 2.0 |
| BHT | 0.01 |
| Root Nodule Extract | 10.0 |
| Water | to 100 |

EXAMPLE 12

To test the ability of a root nodule extract containing leghemoglobin to control nitric oxide levels in human fibroblasts, the following assay was preformed.

Preparation of Fibroblasts

Fibroblasts were seeded into the individual wells of a 6 well plate with an initial cell density of 3,500 cells/cm$^2$ in a total of 2 ml of fibroblast growth medium (FGM). The seeded cells were incubated overnight in an incubator at 37±2° C. and 5±1% $CO_2$. On the following day the FGM was removed via aspiration to eliminate any non-adherent cells and replaced with 2 ml of fresh FGM. The media was changed again every 48 hours of incubation until the cells were fully confluent.

Application of Test Material

The media from the confluent fibroblasts was replaced with the extract described in Example 1, diluted in FGM to yield a final concentration of 1%. Gamma-interferon was used as a positive control (approx 300 U/ml) while untreated cells were used as a negative control. Each condition was tested with 6 replicates. The cells were incubated for 48 hours at 37±2° C. and 5±1% $CO_2$. After the 48-hour incubation the cell culture medium was collected and stored frozen for subsequent assay of nitrite.

Enzymatic Conversion of Nitrate to Nitrite

A 300 µl aliquot of each cell culture medium sample was mixed with 10 µl of a nitrate reductase solution (0.1 U/ml nitrate reductase enzyme, 5 µM FAD, 30 µM NADPH). This mixture was incubated in a water bath (37±2° C.) for at least 15 minutes. To remove any residual NADPH that was not consumed in this initial reaction (the NADPH will interfere with the subsequent Griess Reaction), 10 µl of a lactate dehydrogenase solution (100 U/ml lactate dehydrogenase and 0.3 mM sodium pyruvate) was added and this mixture was allowed to incubate in a water bath (37±2° C.) for at least 5 minutes.

Nitrite Assay: Griess Reaction

A 100 µl aliquot of each cell culture medium sample was added to a well in a 96-well plate. To each aliquot, 50 µl of sulfanilamide solution (1% sulfanilamide in 5% phosphoric acid) was added and the plate was incubated at room temperature for 5 to 10 minutes (protected from light). After this first incubation, 50 µl of NED solution (0.1% N-1-napthyl-ethylenediamine dihydrochloride in $DIH_2O$) was added to each well and the plate was allowed to incubate at room temperature for 5 to 10 minutes (protected from light). After incubating, the absorbance values for each well of the 96-well plate were read at 540 nm.

Nitrite Standard Curve

A nitrite standard curve was generated by performing a series of dilutions with the nitrite standard to generate the following series of concentrations: 100 µM, 50 µM, 25 µM, 12.5 µM, 6.25 µM, 3.13 µM, 1.56 µM, and 0. These samples were diluted in cell culture medium.

Nitrite Assay

To derive the standard curve for the nitrite assay, the absorbance versus the nitrite concentration in μM for the standards was plotted. A linear regression was performed to establish the line that best fits these data points. Mean absorbance values for the test materials and untreated samples were used to estimate the amount of nitrite present in each sample. Using the analysis method it was determined that the extract from the soybean root nodules was able to reduce nitric oxide levels in human fibroblasts by 60% compared to untreated controls.

EXAMPLE 13

To test the ability of a root nodule extract to improve human skin fibroblast viability, a sample of the root nodule extract from Example 4 was tested using the following analytical procedure.

Human fibroblasts were grown to confluence using the method described in Example 10. The fibroblasts were treated with test material following the procedure described in Example 10. After 48 hours of exposure to the test material, the following test was run.

MTT Assay

The cell culture medium was removed and the fibroblasts were washed twice with PBS to remove any remaining test material. After the final wash, FGM supplemented with 2 mg/ml MTT was added to each well and the cells were incubated for approximately 2 hours at approx. $37\pm2°$ C. and $5\pm1\%$ $CO_2$. After the 2-hour incubation, the FGM/MTT solution was removed and the cells were washed again once with PBS and then 2 ml of isopropyl alcohol was added to the well to extract the purple formazin crystals. Two hundred microliters of the isopropyl extracts was transferred to a 96-well plate and the plate was read at 540 nm using isopropyl alcohol as a blank.

MTT Assay

The Mean MTT absorbance values were calculated for the negative control wells. Since these cells were not treated this mean value was used to represent 100% viability (UNTREATED). For the absorbance values in the wells treated with the test material (TREATED samples), the percentage of viable cells was calculated using this equation: [(individual TREATED absorbance)/(mean UNTREATED absorbance)]×100. Using this analytical method, it was determined that the cells treated with the extract from Example 4 had a 30% greater viability than untreated cells showing the extract improved the cell viability of the human skin fibroblasts.

EXAMPLE 14

To test the possibility that a root nodule extract might promote the growth of soluble human elastin, the following study was conducted. A soy root nodule extract was prepared as described in Example 1. The extract and an isotonic saline placebo were buffered to neutral pH with PBS.

Neonatal human fibroblast cells were placed in fibroblast growth medium (FGM) as described above in Example 10 and seeded into culture flasks. The flasks were incubated at 37° C. and 5% $CO_2$ until the cells were fully confluent. The media was changed 24 hours after the initial seeding of the flask to remove any cells that did not survive and then every 48 hours after that. Upon reaching confluency the FGM was removed and the cells were washed once with 9 mls of HEPES Buffered Saline Solution (HEPES-BSS) to remove any residual proteins from the FGM that can neutralize trypsin. Following removal of the HEPES-BSS, 6 ml of Trypsin/EDTA was used to cover the fibroblast monolayer. The trypsin digests the cellular adhesion proteins that hold the fibroblasts to the culture flask while the EDTA chelates any residual calcium to further inactivate the adhesion proteins. Trypsinization did not exceed 3 minutes. After gathering of the cells, 12 ml of trypsin neutralizing solution was added and the released cells were transferred to 15-ml centrifugation tubes. The flask was rinsed with 6 mls of HEPES-BSS to collect residual cells that were added to the previous wash. The centrifuge tubes were then spun at 220×g for 5 minutes to pellet the cells. The supernatant was removed via aspiration and the cells was resuspended in 4 ml of FGM and seeded into 6-well plates. A small aliquot was taken to count the number of cells. The cells were then diluted with FGM to reach a cell density of 17,500 cells/ml. The seeded cells were incubated overnight as described above. On the following day, the FGM was removed via aspiration to eliminate any non-adherent cells and replaced with 2 mls of fresh FGM. The media was changed again every 48 hours of incubation until the cells are fully confluent.

The media of the confluent fibroblasts was replaced with either fresh media or media containing the root nodule extract from Example 1. The cells are then incubated for 48 hours at the same conditions described above.

After the 48-hour incubation period the cell culture medium was collected and the insoluble elastin was extracted from the cells by the addition of 1 ml of 0.25M oxalic acid to the wells that house the fibroblasts. The cells were freed from the plastic wells using a cell scraper and the suspended cells/oxalic acid mixture was added to centrifuge tubes. The tubes were incubated at 95° C. for 60 minutes to solubilize the cells. The tubes were then quickly cooled to RT and centrifuged at 3000 rpm for 10 minutes. The supernatants were combined so that both soluble and insoluble elastins were tested. The supernatant was placed overnight in dialysis tubing with a low molecular weight cut-off (~15,000 MW) to both concentrate the elastin into a smaller volume and to remove the oxalic acid.

A 300 ml aliquot of the sample above was mixed with 1.0 ml of cold Fastin Precipitating Reagent (available from Biocolor, Belfast, Northern Ireland) in a 1.5 ml microcentrifuge tube. The mixture was allowed to incubate for 24 hours at 4° C. to precipitate elastin. The cooled microcentrifuge tubes were spun at 8,000×g for 10 minutes to pack the precipitated elastin. The supernatant was removed by inverting the tube to drain it and then by gently tapping it on an absorbent paper towel.

One (1) ml of Fastin Dye Reagent along with 200 μl of 90% saturated ammonium sulphate was added to each tube. The microcentrifuge tubes were then mixed with a vortex mixer and allowed to incubate for 60 minutes at RT with gentle mechanical agitation. The Fastin Dye Reagent interacts with the amino acids of elastin specifically to form a colored elastin/dye complex that precipitates in the presence of the ammonium sulphate. The microcentrifuge tubes were spun at 8,000×g for 10 minutes to separate the precipitated elastin/dye complex from the unbound dye. The supernatant was carefully removed and the tubes were inverted to drain any residual supernatant.

One (1) ml of Fastin Destain reagent was added to each microcentrifuge tube. The tubes were capped and vortexed as described previously. A 100 ml aliquot from each sample tube was transferred to a 96-well plate and read at 513 nm with a microplate reader. The amount of soluble and insoluble elastin was determined by comparison against a standardization curve prepared from elastin samples supplied by the manufacturer of the Fastin Dye Kit. Using the described methodology, it was found that the cells grown in the presence of the root nodule extract contained statistically greater quantities of elastin than the cells grown in the untreated controls. Fibroblast cell viability was determined as described in Example 11 and the cells were shown to be viable under the conditions of the experiment.

EXAMPLE 15

To test the possibility that an extract from a root nodule containing leghemoglobin can control the production of cyclic-GMP in human skin fibroblasts, the following test was run using the extract produced in Example 2.

cGMP Assay: Fibroblast Cell Culture Preparation and Treatment

Human dermal fibroblasts were seeded at $7.5 \times 10^4$ cells/ml in 1 ml of cell culture medium into the wells of a 12-well tissue culture plate (three wells were prepared for each treatment). After seeding, the cells were incubated overnight at $37 \pm 2°$ C. and $5 \pm 1\%$ $CO_2$. On the next day, the culture medium was removed via aspiration and the cells were incubated for 10 minutes in 400 µl of prestimulation buffer (Stock 800 mM IBMX: 100 mg IBMX dissolved in 563 µl DMSO; prestimulation buffer: 9.4 µl 800 mM IBMX added to 10 ml phosphate buffered saline). After this pretreatment, a 200 µl volume of phosphate buffered saline (negative control), test material+ spermine NONOate (300 mM), or spermine NONOate (300 mM, positive control) were added to each well. It should be noted that there is a dilution at this point so materials to be added were prepared at 3× their intended final concentration (final concentration of spermine NONOate was 100 mM). The cells were then incubated for 1.5 hours at $37 \pm 2°$ C. and $5 \pm 1\%$ $CO_2$. At the end of this treatment period 200 µl of lysis buffer was added to each well and 12-well plate was placed on a rocking platform for 10 minutes at room temperature. The cell lysate was then collected and assayed immediately for cGMP. In addition to the fibroblasts, blank wells were run (wells without cells in them) containing known amounts of cGMP. These samples were treated and collected as described above and used to generate a standard curve for the cGMP assay.

Catchpoint cGMP Assay

The catchpoint cGMP assay is a competitive fluorescence based ELISA assay. In this type of assay, as the amount of cGMP in a sample increases, the fluorescent signal will decrease. The assay procedure is as follows:

1. Fifty (50) µl of each sample to be assayed were added to respective wells in a clear bottom black 96-well plate (these samples include the cGMP samples to be used for a standard curve). The wells in the well plate were previously coated with an anti-rabbit IgG.
2. Fifty (50) µl of a rabbit anti-cGMP antibody were then added to the wells used above.
3. Fifty (50) µl of a cGMP-horse radish peroxidase (HRP) conjugate were then added to each well used above and the well plate was incubated for 2 hours at room temperature on a rocking platform.
4. After the incubation period, the well plate was washed four times with 300 µl of wash buffer (supplied with the kit: 0.02M Tris [pH 7.4], 150 mM CaCl, 0.05% Tween 20, and 0.05% Proclin).
5. After removing the final wash via aspiration, 100 µl of Stoplight Red fluorescent substrate solution (with 1 mM $H_2O_2$) was added to each well used in the well plate and the plate was incubated for at least 1 hour (10 minutes is the minimum incubation time, but the signal is stable for up to 24 hours). During this incubation period the 96-well plate was protected from light.
6. After the incubation period, the 96-well plate was read using a Fluoroskan Ascent F/L plate reader at these setting:
   a. Excitation filter: 530 nm
   b. Emission filter: 590 nm
   c. Integration time: 50 msec CGMP Assay To quantify the amount of cGMP present, a standard curve was generated using known concentrations cGMP. A regression analysis was then performed to establish the line that best fits these data points. Cyclic CMP content in the samples treated via the various conditions was then estimated via this standard curve. Using this analysis method, it was found that fibroblasts treated with 100 mM of Spermine NONOate showed an increased production of c-GMP of almost 80%. Treatment of the same fibroblasts with 100 mM of Sperimine NONOate containing 10% of the root nodule extract from Example 2 reduced the levels of c-GMP back down to levels noted for untreated cells showing the extract has an ability to control c-GMP levels in human fibroblasts.

EXAMPLE 16

To test the possibility that an extract from a root nodule containing leghemoglobin could influence melanogenesis (tanning) in human skin, the following in vitro test was performed using the extract taken from Example 2.

Tissue Preparation

Upon arrival, the MatTek Melanopenn tissues were stored at 4° C. until used. Prior to use, the tissues to be used were removed from the agarose-shipping tray and placed into a E-well plate containing 0.9 ml of assay medium ($37 \pm 2°$ C.). All of the agarose was removed from the outside of the tissue culture insert since any residual agarose may prevent the assay medium from reaching the tissue. The tissues were allowed to incubate for at least 1 hour at $37 \pm 2°$ C. and $5 \pm 1\%$ $CO_2$. After this initial incubation, the assay medium was replaced with 5.0 ml of fresh medium ($37 \pm 2°$ C.) and the tissues inserts were placed on 2 sterile stainless steel washers to raise the level of the bottom of the insert such that it touched the surface of the assay medium.

Application of Test Material

Twenty-five (25) µl or mg of test material was applied directly onto the surface of the tissue. In addition to the test material, a positive ($10^{-7}$M alpha melanocyte stimulating hormone and 3 ng/ml bFGF in the assay medium) and negative (no treatment) control was also applied to respective tissues. The 6-well plates were then incubated at $37 \pm 2°$ C. and $5 \pm 1\%$ $CO_2$ and identical sets of plates were incubated for 10 days and 17 days. During this incubation period, the tissues were rinsed and new test material was applied and the assay medium changed every other day.

Macroscopic Observation

At the end of the incubation period, the assay medium in some of the 6-well plates was replaced with 0.9 ml of PBS and the stainless steel washers were removed. The 6-well plates containing the tissue were placed under an inverted microscope and the tissues were evaluated to determine if the test material had exerted any cytotoxic effects on the melanocytes. Toxic effects would be indicated by melanocytes that had a rounded up and/or non-dendritic morphology. After the macroscopic evaluation, the Melanoderm tissues were removed from the culture inserts and stored at $-75 \pm 5°$ C. until assayed for melanin content.

Melanin Extraction from Tissues

Two frozen tissues for each treatment and time point were pooled and homogenized in 0.45 ml of 1% SDS containing 0.05 mM EDTA and 10 mM Tris (pH 6.8). Twenty (20) μl of a 5 mg/ml Proteinase K solution was then added to each homogenate and the mixture was allowed to digest overnight in a water bath set at 45±2° C. After the overnight digestion, an additional 20 μl of 5 mg/ml Proteinase K was added to each homogenate and the mixture was allowed to digest for an additional 4 hours (or longer-until no clumps of tissue remain). After the digestion, 50 μl of 500 mM sodium carbonate was added to make the digest basic, followed by the addition of 10 μl of 30% hydrogen peroxide. The samples were then incubated at 80±2° C. for 30±5 minutes and then cooled to room temperature. After cooling, 100 μl of a chloroform/methanol (2:1) mixture was added to each sample. The sample was then centrifuged for 10 minutes at 10,000×g). The top phase of each sample was collected and its absorbance at 405 nm was determined via a 96-well plate reader.

Melanin Standard

Known concentrations of synthetic melanin were taken through the extraction process described above. The absorbance values of these known concentrations were used to generate a standard curve of melanin concentrations.

The absorbance values for the melanin standards were plotted against their respective concentrations to generate a standard curve. The equation that best fits this curve was then determined via regression analysis and this equation was used to calculate the melanin concentrations of the unknown samples. The tissue melanin concentrations were then compared using a two-factor analysis of variance (using treatment and time point as the two factors). It was found that the tissue sample treated with the extract taken from Example 2 showed a statistically significant reduction in melanin concentration verses an untreated control.

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A personal care composition selected from the group consisting of soaps, shampoos, skin care medicaments, cosmetics, and therapeutic formulations consisting essentially of:
    (a) leghemoglobin extracted from nitrogen fixation root nodules,
    (b) at least one preservative selected from the group consisting of phenoxyethanol, benzyl alcohol, methyl paraben, propyl paraben, butyl paraben, benzalkonium chloride, methylisothiazolinone, methylchloroisothiazolinone, DMDM hydantoin, imidazolidinyl urea, diazolidinyl urea, butylated hydroxytoluene, tocopherol, triclosan, chlorohexidine digluconate and combinations thereof, and
    (c) a surfactant,
    wherein said leghemoglobin is present in a concentration of between about 0.0001% and about 10% based upon the total weight of the composition.

2. The personal care composition of claim 1 wherein said leghemoglobin is encapsulated within a liposome or a maltodextrin encapsulating oligosaccharide in order to provide a time-release characteristic to said leghemoglobin.

3. The composition of claim 1 which additionally contains water.

4. The composition of claim 1 having a form selected from the group consisting of lotions, ointments, creams, sprays, spritzes, aqueous mixtures, aqueous alcoholic mixtures, gels, mousses, patches, pads, masks, moistened cloths, moistened wipes, solid sticks, clear sticks, lipsticks, aerosol creams, anhydrous powders, talcs, tonics, oils, emulsions, and bath salts.

* * * * *